United States Patent [19]

Dutta et al.

[11] Patent Number: 5,066,403

[45] Date of Patent: Nov. 19, 1991

[54] PROCESS FOR SEPARATING AZEOTROPIC OR CLOSE-BOILING MIXTURES BY USE OF A COMPOSITE MEMBRANE, THE MEMBRANE, AND ITS PROCESS OF MANUFACTURE

[75] Inventors: Binay K. Dutta, Calcutta, India; Subhas K. Sikdar, Boulder, Colo.

[73] Assignee: The United States of America as represented by the Secretary of Commerce, Washington, D.C.

[21] Appl. No.: 551,342

[22] Filed: Jul. 12, 1990

[51] Int. Cl.⁵ .............................................. B01D 61/36
[52] U.S. Cl. ................................... 210/638; 210/640; 210/500.36; 427/245
[58] Field of Search .................... 210/640, 500.36, 638; 427/245, 246; 264/41, 49

[56] References Cited

U.S. PATENT DOCUMENTS

| | | | |
|---|---|---|---|
| 4,035,291 | 7/1977 | Chiang et al. | 210/640 X |
| 4,470,859 | 9/1984 | Benezra et al. | 156/155 |
| 4,663,013 | 5/1987 | Kumagai et al. | 204/296 |
| 4,728,429 | 3/1988 | Cabasso et al. | 210/638 |
| 4,778,596 | 10/1988 | Linder et al. | 210/638 |
| 4,902,416 | 2/1990 | Schroeder et al. | 210/321.74 X |

FOREIGN PATENT DOCUMENTS 58-58104  4/1983  Japan .

OTHER PUBLICATIONS

Aptel et al., *J. Memb. Sci.*, 1 (1976), pp. 271–287.

Cabasso I., *Ind. Eng. Chem. Prod. Res. Dev.*, 22 (1983), pp. 313–319.

*Primary Examiner*—Frank Spear
*Attorney, Agent, or Firm*—Thomas Zack; Thomas P. Pavelko

[57] ABSTRACT

The present disclosure is directed to composite membranes formed by casting a thin (about 8 to about 20 microns) film of perfluorosulfonic acid (PFSA) polymer on a porous matrix of polytetrafluoroethylene (PTFE). The ion exchange groups in these membranes are protons and can be substituted with metal ions such as $Na^+$, $Ca^+$, $Ag^+$, etc. or by organic ligands. Alternatively, even thinner membranes (from about 1 micrometer or thinner up to 20 micrometers) can be formed by spraying a PPSA polymer solution on a porous matrix. The porous matrix may comprise polytetrafluoroethylene alone or in combination with a thermobonded polypropylene support.

Both the acid and the substituted membranes have remarkable affinity for polar compounds or mixtures of polar and non-polar compounds such that azeotropic mixtures of organic compounds as well as close-boiling liquid mixtures can be easily separated at good permeation rates using the technique of pervaporation.

The membrane of the present invention gives considerably higher fluxes while maintaining good separation factors. The method of the preparation of the membrane is simple and the resulting membrane is mechanically strong.

18 Claims, 2 Drawing Sheets

PROCESS FOR SEPARATING AZEOTROPIC OR CLOSE-BOILING MIXTURES BY USE OF A COMPOSITE MEMBRANE, THE MEMBRANE, AND ITS PROCESS OF MANUFACTURE

The invention described herein may be manufactured, used and licensed by or for the Government for Governmental purposes without the payment to us of any royalties thereon.

BACKGROUND OF THE INVENTION

1. Field of the Invention

The present invention is directed t the separation of organic liquid mixtures. The separation of organic liquid mixtures is a common operation in many process industries, especially in the petrochemical industry. When applied to separating close-boiling mixtures, fractional distillation, the conventional technique for separating organic liquid mixtures, is expensive on account of its large energy usage. Frequently, many equilibrium stages, coupled with a large reflux ratio, would be required in order to effect the desired degree of separation. To separate constant boiling binary azeotropic mixtures into their components in substantially pure form, distillation requires adding a third component, and requires the use of more than one column. An example of such a distillation is the process of making absolute ethanol (100%) from a constant boiling azeotropic composition of 95.5% ethanol and 4.5% water. As a third component, benzene is added to the mixture. The resulting distillate produces two liquid layers, one containing practically no water and the other containing most of the water. The use of benzene in such a process not only increases the cost of raw materials, but also entails an additional handling step as well as introducing a potentially environmentally hazardous material into the process.

By contrast, a membrane-based process offers an effective and low-cost alternative to separating close-boiling liquid mixtures by distillation.

In recent years several alternative separation strategies, such as pervaporation, perstraction, and membrane distillation have been suggested. However, the application of any of these techniques depends on finding a suitable membrane for the particular separation problem. For pervaporation —which may be defined as the preferential dissolution in, and permeation through, a membrane of one or more components of a mixture, and removal of the permeate material from the other side of the membrane by evaporation—proceeds through a sorption-diffusion-desorption type mechanism, with the effectiveness of a particular membrane for a given mixture being dependent on the interaction between the membrane and the components present in the mixture.

For the first time, the present invention provides membranes which facilitate a process of separating close-boiling liquids or azeotropic liquid mixtures, as well a novel process of manufacture of such membranes.

2. Description of Related Art

Few publications mention the separation of organic azeotropes using polymeric membranes. In Aptel et al, *J. Memb. Sci.*, 1 (1976), pages 271–287 is described a pervaporation process through poly(tetrafluorethylene) film grafted with N-vinylpyrrolidone to fractionate positive azeotropic liquid systems. Selectivities higher than 10 have reportedly been obtained and daily productions above 100 kg per square meter of membrane have been reported. The pervaporation flux, ($\phi$), expressed in kg/hour per meter squared of membrane, was quite low. Other attempts for separating close-boiling, heat sensitive mixtures are set forth in U.S. Pat. No. 4,728,429 which also contains a description of various prior art membrane-forming materials and processes at columns 1–3 of its disclosure. It is quite evident from the description of these various prior art membrane-forming materials and processes of use that the art is searching for a membrane which is not only highly selective but also permits high pervaporation flux so as to facilitate the utilization of the membrane in a commercial process for separation of close-boiling liquids and/or liquid azeotropic mixtures. Other disclosures of membrane compositions and the use of such membranes can be found in the following publications: Cabasso I., *Ind. Eng. Chem. Prod. Res. Dev.*, 22 (1983), pages 313–319; Japanese Patent 58 58 104, issued to Kuraray Co. Ltd. Sin-Etsu Chem. Industry Co. Ltd., on Apr. 6, 1983, and U.S. Pat. Nos. 4,470,859, 4,663,013 and 4,778,596. The disclosures of each of the above-mentioned publications and patents are herein incorporated, by reference, in their entireties.

From the activity in this area, as represented by the foregoing publications and patents, it is evident that a long felt and continuing need for novel membranes is required in order to successfully separate organic liquid mixtures, especially close-boiling liquids and azeotropic liquid mixtures in a commercially feasible process. The membranes of the present invention are formed by a unique process of manufacture.

SUMMARY OF THE INVENTION

The present invention provides composite membranes of various polymeric materials, having both high selectivity and high pervaporation flux, as compared to the membranes of the prior art. Additionally, applicants have discovered new processes of manufacturing the novel membranes according to the present invention which yield membranes having considerably higher fluxes, as compared to membranes of the prior art, while maintaining good separation. The method of preparation of the membranes of the invention is simple and produces a membrane which is not only mechanically strong but one which may be used in various organic media.

The membranes made according to the presently disclosed invention can be converted from the acid form to the substituted form simply by soaking the acid membrane in solutions of the substituents. The proton in the acid membrane can be replaced by metal ions or other inorganic or organic substituents to tailor the properties of the membranes to separate either various close-boiling liquids or azeotropic liquid mixtures.

The present invention also provides an improved process of separating close-boiling liquids and liquid azeotropic mixtures at high pervaporation fluxes of organic permeants with the highest attendent selectivities ever reported.

These and other attributes of the invention will become apparent from the following detailed description of the preferred embodiments of the invention.

DETAILED DESCRIPTION OF PREFERRED EMBODIMENTS

Figure 1:
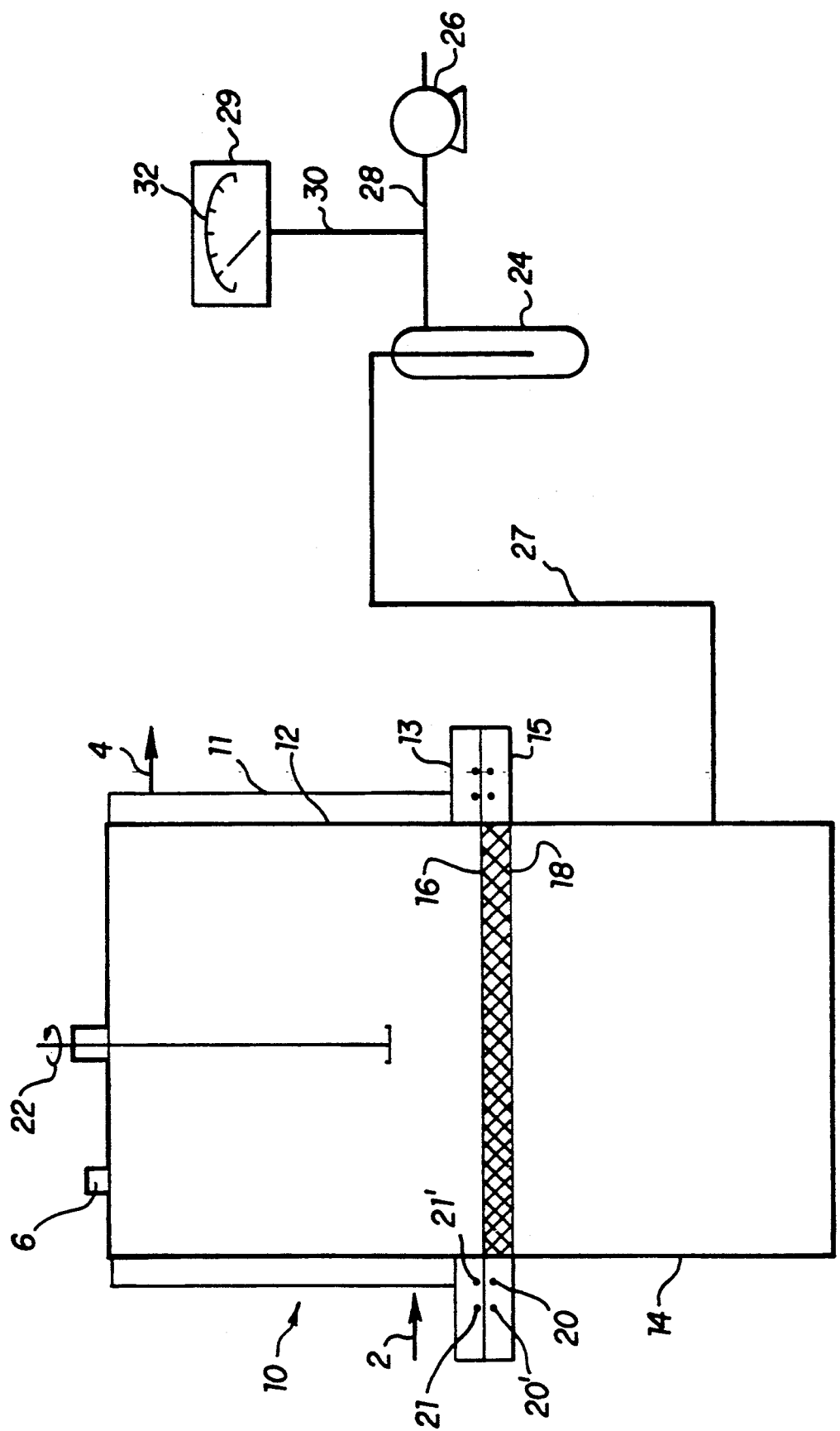
FIG. 1 is a schematic view of a permeation cell used for practicing pervaporation utilizing a membrane of the present invention.

The present invention provides composite membranes which can be used for separating azeotropic mixtures and/or close-boiling liquids as are frequently encountered in petrochemical and organochemical industries. Such mixtures include organic mixtures (binary or having more than two components). Typical of the azeotropic mixtures of organic compounds, especially polar organic compounds, are benzenecyclohexanol, isopropyl alcohol-cyclooxane, ethanol-water, etc. Both the acid and the substituted membranes of the present invention were found to have remarkable affinity for such polar organic compounds. Other compounds such as mixtures of polar and non-polar compounds can also be separated according to the discoveries of the present invention. In the following description, all percentages (%) are by weight, unless otherwise noted.

The novel membranes of the present invention comprise a thin, i.e., from less than about 1 to about 20 microns, film of a perfluorosulfonic acid (PFSA) polymer on a porous matrix of polytetrafluoroethylene (PTFE). The ion exchange groups in these membranes are protons which can be substituted with metal ions selected from the Group VI B and VIII B elements of the Periodic Table. Particularly preferred ions are Na+, Cs+, Ag+, etc. Alternatively the membranes can be substituted by organic substituents such as organic ligands. Particularly preferred are quaternary ammonium salts, diamines, $NH_2-R-NH_2$, such as ethyldiamine or mercaptoamines, $NH_2-R-SH_2$, wherein R is any alkyl having one or more carbon atoms.

These membranes can be manufactured by coating the PTFE backing material with a commercially available solution of a PFSA polymer, air-drying the film and subsequently curing the composite for a few hours (depending on the thickness of the film) at about 100° C. to about 160° C. Preferably, membranes formed by casting are annealed or cured at temperatures from about 110° C. to about 160° C. The resulting material was insoluble in most solvents but swelled greatly in polar organic solvents, like alcohols. The membrane swelled or interacted little with non-polar liquids like hydrocarbons. While the film of the ion exchange polymer had considerable mechanical strength in itself, the backing material imparted additional durability to the composite.

In applicants' attempts to cast thin, discriminating, films on supports, initial trials with porous supports, such as polypropylene, cellulose acetate, or a nylon net, yielded poor adhesion of the membrane film to the support. Applicants found that thin, porous PTFE films provided good support for the composite membrane. The resulting membrane proved to be not only durable but also exhibited good mechanical strength.

For casting the composite membrane, applicants did not dissolve the commercial membrane material to prepare the casting solution. Instead, applicants used a commercially available 5% solution of a perfluorosulfonic acid polymer of 1100 equivalent mass, in a mixture of a lower aliphatic alcohol and water. Other solutions of perfluorosulfonic acid polymer of from about 1 to about 20% may be employed in the invention without departing from the spirit thereof. A water-soaked piece of PTFE support film was stretched on a flat support, e.g., a glass plate. PTFE is strongly hydrophobic and will soak water only with difficulty. Therefore, the PTFE support was first soaked in methanol which was then replaced by warm water over a period of about half an hour. A measured volume of the PFSA polymer solution was spread uniformly over the support film thus prepared. The thickness of the solution layer was controlled by rolling a glass rod over the liquid layer and maintaining a uniform gap between the support film and the rod. The PFSA solution, after evaporating at room temperature, left a thin layer of the PFSA polymer over the support. The material was then annealed for one hour by placing the glass plate on a hot surface maintained at about 105° C. The composite membrane was removed from the glass plate by dipping in cold water. No casting reagent, like dimethylformamide or cyclohexanol, was necessary for making the membrane. However, such reagents are needed to cast thin films of PSFA polymers without a support matrix.

Annealing the air-dried composite was a critical step in preparing the membranes of the present invention. In the perfluorosulfonated polymer film, phase separation is thought to occur between the hydrophobic fluorocarbon backbone and the hydrophilic sulfonic acid group. The membrane swells in contact with solvents, such as lower aliphatic alcohols and water. At temperatures higher than room temperature, the forces among the fluorocarbon chains are weakened, resulting in phase inversion of the fluorocarbon and the ionic cluster. During annealing, it is thought the fluorocarbon chains and the polymer film again fused together to form a durable and insoluble layer.

Figure 2:
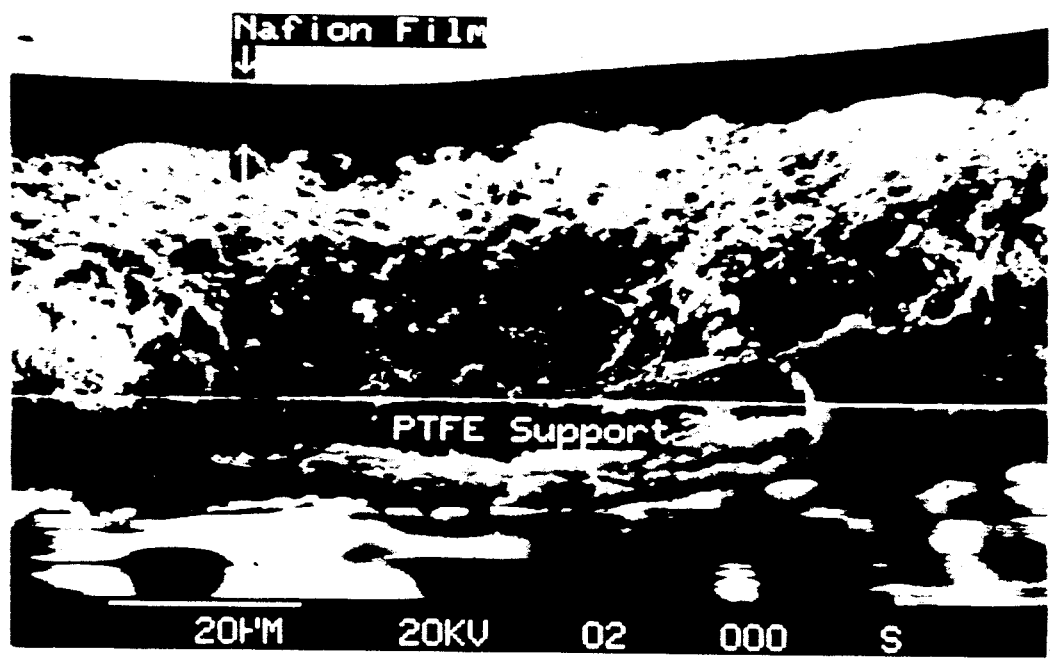
FIG. 2 is a scanning electron micrograph (SEM) of a composite membrane formed by one embodiment of the present invention.

Referring now to FIG. 2 which shows a scanning electron micrograph (SEM) of the cross-section of a composite membrane, as formed (cast) by the above-described procedure. The black top layer, about 10 microns thick, is the discriminating layer for separation. The thickness of the film can be controlled by controlling the PFSA concentration in the casting solution.

Figure 3:
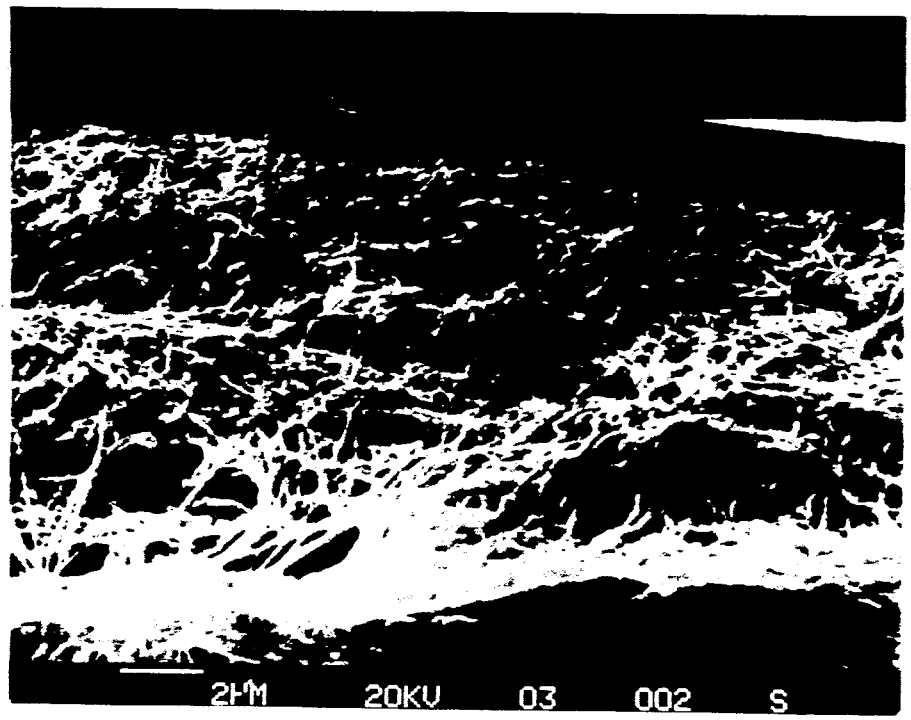
FIG. 3 is an SEM of a composite membrane formed according to an alternative embodiment of the present invention.

An alternative method of manufacturing the composite membrane according to the present invention can be achieved by a spray technique which generally provides much thinner PFSA skins than the casting procedure described above. As noted in FIG. 3, which is an SEM of a non-porous PFSA film, of about 2 micrometer thickness, on a highly porous PTFE film made according to a spray technique method of manufacture, the spray technique is suitable for forming membranes of much reduced thickness. Thicknesses of less than 1 micrometer can be obtained by this process. Preferably, the membranes formed by spraying are annealed at temperatures from about 100° C. to about 105° C. In FIG. 3, the commercial support itself had two layers: a polypropylene matte backing (fibrous) attached to a porous PTFE film. A non-porous PFSA film is illustrated on top. The thermobonded polypropylene support cannot be seen in the SEM of FIG. 3.

The best mode of manufacturing thin membranes according to the present invention will be illustrated in the following example.

EXAMPLE 1

A 0.1 m×0.1 m support membrane (76 micrometer PTFE film thermobonded to a polypropylene matte, Tradename TETRATEC) is first soaked in methanol for one hour and later in distilled water for one additional hour. It is then spread flat on a glass sheet, and water drops from its surface are wiped off. 1-2 ml of a 5% solution of a commercially available PFSA is evenly sprayed on the membrane surface using an artist's spray gun operated with pressurized nitrogen. Three hours after spraying, the composite membrane is annealed at 100°-120° C. for one hour. The resulting membrane had a PFSA film thickness of 2 micrometers.

EXAMPLE 2 process of pervaporation

In order to demonstrate a process of separating close-boiling mixtures, reference will be had to the schematic presentation of a process as set forth in FIG. 1. A stainless steel jacketed permeation cell 10 provided with two compartments 12, 14 is illustrated in FIG. 1. Compartment 14, which is illustrated as the lower compartment in FIG. 1, has a stainless steel disk support 16 for supporting a membrane 18. The stainless steel disk support 16 is held between flange 13 of the upper compartment and flange 15 of the lower compartment. A series of 0-rings, generally illustrated at 20, 20', 21, 21' assure the sealing of upper compartment 12 to lower compartment 14. Upper compartment 12 contains a feed solution which is subjected to mechanical stirring imparted by stirrer 22. A pervaporate was withdrawn from lower compartment 14 by applying a vacuum (0.3 mm Hg) which was collected in a liquid nitrogen trap 24 placed between permeation cell 10 and vacuum pump 26. Conduits 27 and 28 connected permeation cell 10 to the liquid nitrogen trap 24 and vacuum pump 26, respectively. A vacuum gauge 29 is connected through conduit 30 to conduit 28. The degree of vacuum drawn on the system can be read from indicator 32 of vacuum gauge 29.

In use, a close-boiling liquid can be fed through inlet 2 of upper compartment 12 with the effluent being withdrawn from compartment 12 via outlet 4. A thermometer port 6 is provided for insertion of a thermometer (not shown) into upper compartment 12. The upper compartment 12 is provided with a water jacket 11 so as to control the temperature of the close-boiling mixture in upper compartment 12. In the apparatus just described, various alcohol-hydrocarbon systems were tested, both with a membrane in the acid form as well as a membrane in the substituted Na+ form with the results being found in Table 1 below. In each case, a membrane produced by the casting process described hereinabove was utilized.

TABLE 1

A. Membrane in the Acid Form

| System | Temp | Flux (kg/h · m²) | Sep. Factor for alcohol |
|---|---|---|---|
| ethanol/cyclohexane (30.7 mol % methanol) | 45° C. | 2.16 | 24.3 |
| ethanol/cyclohexane (37.6 mol % ethanol) | 45° C. | 2.87 | 14.8 |

B. Membrane in Na+ Form

System: Ethanol/Cyclohexane

| Temp | Composition, mol % ethanol | | Flux |
|---|---|---|---|

TABLE 1-continued

| Temp | feed | product | kg/hr · m² |
|---|---|---|---|
| 55° C. | 43% (azeotropic) | 97% | 0.56 |
| 55° C. | 64% | 97% | 0.78 |

EXAMPLE 3

A 0.1 m×0.1 m support membrane (76 micrometer PTFE film thermobonded to a polypropylene matte, Tradename TETRATEC) is first soaked in methanol for one hour and later in distilled water for one more hour. It is then spread flat on a glass sheet, and water drops from its surface are wiped off. 1-2 ml of a 5% solution of PFSA, the solution being commercially available, is evenly sprayed on the membrane surface using an artist's spraygun operated with pressurized nitrogen. Three hours after spraying, the composite membrane is annealed at 100°-120° C. for one hour.

From the foregoing description of the preferred embodiments, it is evident that thin membranes of high selectivity and pervaporation flux can be formed having good mechanical strength which permits the commercial utilization of pervaporation techniques for separating close-boiling liquids and/or azeotropic mixtures. The membranes of the invention are easy to convert from the acid form to the substituted form as desired for specific applications and are suitable for use in various organic media. The membranes of the present invention are the thinnest composite ion exchange membranes of the PFSA type ever reported and provide unexpectedly superior separation rates without loss of mechanical strength and have unexpectedly superior selectivity in separating close-boiling liquids and/or azeotropic mixtures. Either polar or non-polar components can be separated.

It should be understood, of course, that the foregoing disclosure relates to only preferred embodiments of the invention and that it is intended to cover all changes and modifications of the examples which do not constitute departures from the spirit and scope of the invention as set forth in the appended claims.

We claim:

1. An integral composite pervaporation membrane exhibiting high pervaporation flux comprising a porous hydrophobic polytetrafluoroethylene matrix substrate having adhered to at least one side thereof a thin ion exchange membrane.

2. The composite membrane of claim 1 wherein the ion exchange membrane has a thickness of less than about 1 to about 20 microns.

3. The composition membrane of claim 1 wherein the ion exchange membrane comprises a perfluorosulfonic acid polymer.

4. The composite membrane of claim 1 having a porous layer bonded to at least one side of the porous matrix substrate opposite the side to which is adhered the thin ion exchange membrane.

5. The composite membrane of claim 1 wherein the ion exchange membrane is in acid form.

6. The composite membrane of claim 1 wherein the ion exchange membrane is in substituted form.

7. The use of the membrane of claim 1 to separate close-boiling liquids or liquid azeotropic mixtures comprising the steps of:

brining the liquid to be treated into contact with the ion exchange membrane;

the ion exchange membrane providing a high pervaporation flux across the membrane; and, removing a separated liquid of high purity.

8. The process of claim 7 wherein the azeotropic mixtures comprise a polar organic compound in admixture with at least one polar or non-polar compound.

9. The process of claim 7 wherein a vacuum is drawn on the side of the ion exchange membrane opposite the ion exchange material.

10. The process of claim 7 wherein the ion exchange material is in acid form.

11. The process of claim 7 wherein the ion exchange material is in substituted form.

12. The process of claim 7 wherein the liquid mixture is selected from the group consisting of ethanol-water; ethanol-cyclohexane; benzene-cyclohexanol; and isopropylalcohol-cyclooxane.

13. A process of manufacturing an integral composite membrane comprising the steps of:

providing a porous hydrophobic matrix comprising polytetrafluoroethylene;

applying a solution comprising a perfluorosulfonic acid polymer to form a film on said porous matrix;

air drying the film; and subsequently curing the composite at a temperature from about 100° C. to about 160° C.

14. The process of claim 13 wherein the solution containing the perfluorosulfonic acid polymer is cast on the porous matrix.

15. The process of claim 13 wherein the solution containing the perfluorosulfonic acid polymer is sprayed on the porous matrix.

16. The process of claim 13 wherein the film is substituted with ions selected from the group consisting of the Group VI B, VIII B elements of the Periodic Table, and organic ligands.

17. A process of manufacturing a composite membrane comprising the steps of:

providing a porous matrix comprising polytetrafluoroethylene;

applying a solution comprising a perfluorosulfonic acid polymer to form a film on said porous matrix;

air drying the film; and subsequently curing the composite at a temperature from about 100° C. to about 160° C.

wherein the perfluorosulfonic acid solution comprises a 1-20% solution of a perfluorosulfonic acid polymer in an aqueous mixture of a lower aliphatic alcohol.

18. A process of manufacturing a composite membrane comprising the steps of:

providing a porous matrix comprising polytetrafluoroethylene;

applying a solution comprising a perfluorosulfonic acid polymer to form a film on said porous matrix;

air drying the film; and subsequently curing the composite at a temperature from about 100° C. to about 160° C.

wherein the polytetrafluoroethylene is first soaked in methanol, which is then replaced with water, and stretched over a flat support before the solution containing the perfluorosulfonic acid polymer is applied thereon.

* * * * *